US011963758B2

(12) United States Patent
Olson et al.

(10) Patent No.: US 11,963,758 B2
(45) Date of Patent: *Apr. 23, 2024

(54) SYSTEM AND DEVICE FOR NON-INVASIVE DRINK DETECTION

(71) Applicant: HAPPY HEALTH, INC., Austin, TX (US)

(72) Inventors: Byron P. Olson, Boone, IA (US); Nithin O. Rajan, Austin, TX (US); Lane Musgrave, Austin, TX (US); David E. Clift-Reaves, Austin, TX (US); James Breaux, Austin, TX (US); Dustin M. Freckleton, Austin, TX (US); Paulo E. Xavier Da Silveira, Boulder, CO (US)

(73) Assignee: Happy Health Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/301,653

(22) Filed: Apr. 17, 2023

(65) Prior Publication Data
US 2023/0248265 A1 Aug. 10, 2023

Related U.S. Application Data

(63) Continuation of application No. 16/643,454, filed as application No. PCT/US2018/048882 on Aug. 30, 2018, now Pat. No. 11,627,892.
(Continued)

(51) Int. Cl.
*A61B 5/11* (2006.01)
*A61B 5/00* (2006.01)
(Continued)

(52) U.S. Cl.
CPC ............ *A61B 5/1114* (2013.01); *A61B 5/01* (2013.01); *A61B 5/02055* (2013.01);
(Continued)

(58) Field of Classification Search
CPC ...... A61B 5/1114; A61B 5/01; A61B 5/02055; A61B 5/02416; A61B 5/02438;
(Continued)

(56) References Cited

U.S. PATENT DOCUMENTS

| 2010/0081960 A1* | 4/2010 | McKenna | A61B 5/4869 600/547 |
| 2015/0071518 A1* | 3/2015 | Campagna | G16H 30/40 382/131 |

(Continued)

FOREIGN PATENT DOCUMENTS

| JP | 2000245713 A | 9/2000 |
| WO | 2019046596 A1 | 3/2019 |

OTHER PUBLICATIONS

International Search Report and Written Opinion; PCT Application No. PCT/US2018/048882; dated Nov. 19, 2018.
(Continued)

*Primary Examiner* — Amine Benlagsir
(74) *Attorney, Agent, or Firm* — Polsinelli PC

(57) ABSTRACT

A wearable device is provided. The wearable device includes at least one motion sensor operable to detect one or more motion signals, a processor coupled to the at least one motion sensor, one or more biological sensors coupled to the processor and operable to detect one or more biological indicators of a user, and a memory configured to store instructions executable by the processor. The instructions, when executed, are operable to: obtain at least one of the one or more biological indicators of the user; correlate the at least one biological indicators of the user with the detected one or more motion signals; and determine that a drink event is detected based on the correlation between the detected one or more motion signals and the at least one biological indicators.

17 Claims, 9 Drawing Sheets

Related U.S. Application Data

(60) Provisional application No. 62/553,655, filed on Sep. 1, 2017.

(51) Int. Cl.
| | |
|---|---|
| *A61B 5/01* | (2006.01) |
| *A61B 5/0205* | (2006.01) |
| *A61B 5/024* | (2006.01) |
| *A61B 5/0537* | (2021.01) |
| *A61B 5/1455* | (2006.01) |
| *G06F 1/16* | (2006.01) |
| *G06N 20/00* | (2019.01) |
| *G16H 20/60* | (2018.01) |

(52) U.S. Cl.
CPC ...... *A61B 5/02416* (2013.01); *A61B 5/02438* (2013.01); *A61B 5/0537* (2013.01); *A61B 5/1112* (2013.01); *A61B 5/14551* (2013.01); *A61B 5/7267* (2013.01); *G06F 1/163* (2013.01); *G06N 20/00* (2019.01); *G16H 20/60* (2018.01)

(58) Field of Classification Search
CPC . A61B 5/0537; A61B 5/1112; A61B 5/14551; A61B 5/7267; A61B 5/0205; A61B 5/024; A61B 5/02405; A61B 5/0533; A61B 5/0816; A61B 5/11; A61B 5/1123; A61B 5/0075; A61B 5/0261; A61B 5/4845; A61B 5/4875; A61B 5/6801; A61B 2503/10; G06F 1/163; G06N 20/00; G16H 20/60
See application file for complete search history.

(56) References Cited

U.S. PATENT DOCUMENTS

| | | | |
|---|---|---|---|
| 2015/0088431 A1* | 3/2015 | Podhajsky | A61B 5/443 600/479 |
| 2015/0224018 A1* | 8/2015 | Graindorge | A61B 5/024 601/46 |
| 2015/0360927 A1* | 12/2015 | Sweeney | G01B 21/22 222/41 |
| 2016/0007934 A1* | 1/2016 | Arnold | A61B 5/1118 600/595 |
| 2016/0038036 A1* | 2/2016 | Augustine | G01K 1/165 600/549 |
| 2016/0055316 A1 | 2/2016 | Jafari et al. | |
| 2016/0220184 A1* | 8/2016 | Manion | A61B 5/4266 |
| 2017/0071518 A1 | 3/2017 | Xavier Da Silveira et al. | |
| 2017/0071551 A1* | 3/2017 | Jain | A61B 5/4884 |
| 2017/0220772 A1* | 8/2017 | Vleugels | A61B 5/0022 |
| 2017/0367639 A1 | 12/2017 | Findlay et al. | |
| 2017/0367939 A1* | 12/2017 | Thomson | A61K 8/27 |
| 2018/0061221 A1* | 3/2018 | He | A61B 5/0015 |
| 2018/0322255 A1* | 11/2018 | Connell, II | G16H 50/20 |

OTHER PUBLICATIONS

International Preliminary Report on Patentability for International Application No. PCT/US2018/048882, dated Mar. 12, 2020, 9 pages.

Amft et al., "Recognition of Dietary activity events using on-body sensors," Artificial Intelligence in Medicine Elsevier, NL, vol. 42, No. 2, Jan. 31, 2008 (Jan. 31, 2008), pp. 121-136.

Extended European Search Report for Application No. EP18850994.7, dated Mar. 12, 2021, 8 Pages.

Kalantarian Haik et al., "A Wearable Nutrition Monitoring System," 2014 11th International Sonference on Wearable and Implantable Body Sensor Networks, IEEE, Jun. 16, 2014 (Jun. 16, 2014), pp. 75-80.

* cited by examiner

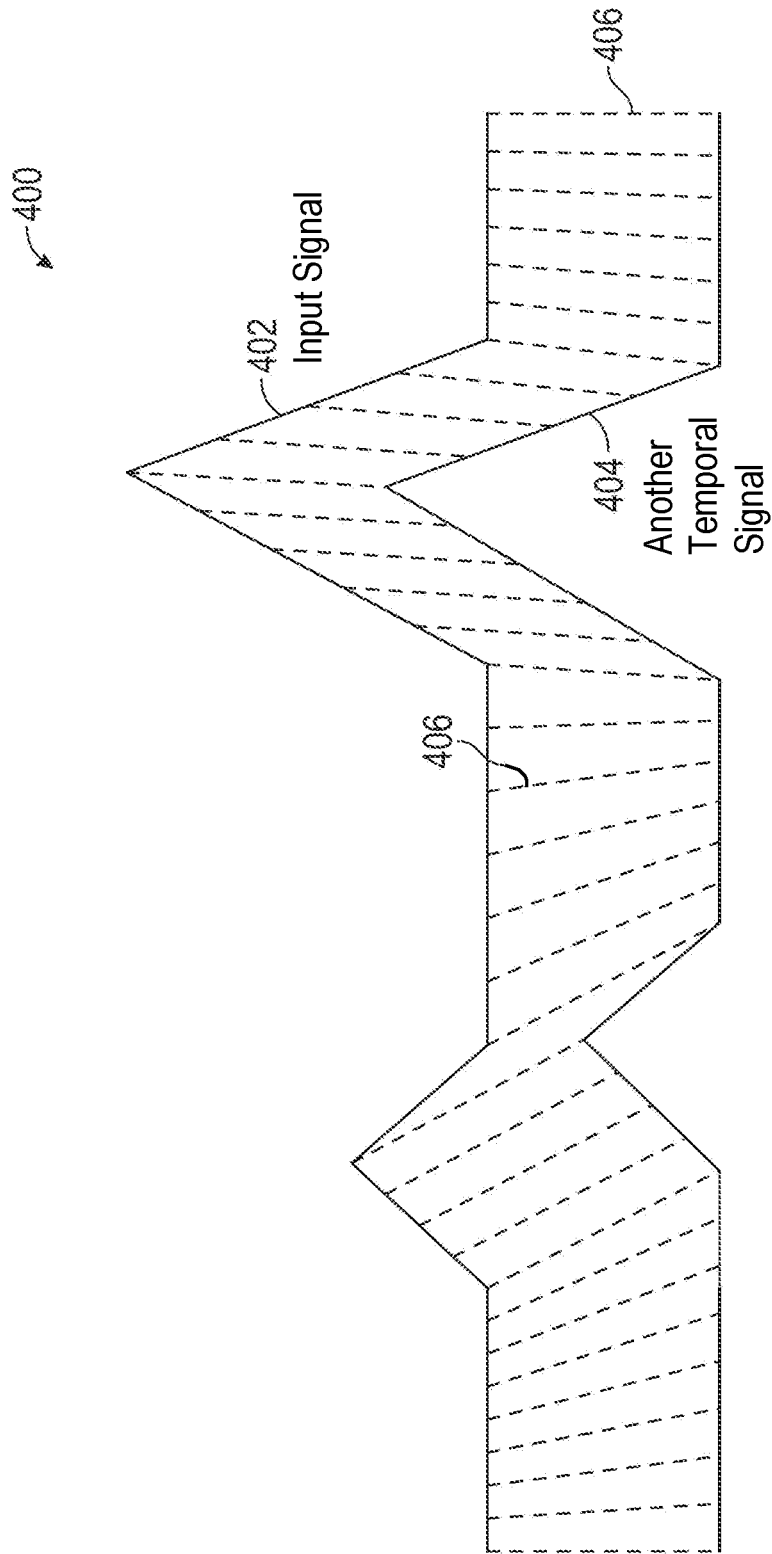

SYSTEM AND DEVICE FOR NON-INVASIVE DRINK DETECTION

CROSS-REFERENCE TO RELATED APPLICATION

This application is a continuation of U.S. Non-Provisional application Ser. No. 16/643,454 filed Feb. 28, 2020, which is a national stage entry of PCT/US2018/048882 filed Aug. 30, 2018, which claims benefit to to U.S. Provisional Patent Application No. 62/553,655, which was filed in the U.S. Patent and Trademark Office on Sep. 1, 2017, each of which is incorporated herein by reference in its entirety for all purposes.

FIELD

The present disclosure relates to systems and devices related to the non-invasive drink detection. In particular, the present disclosure relates to systems and devices operable to detect whether a user is drinking a substance.

BACKGROUND

Wearable devices have been used by performance athletes and amateurs to monitor physical activities. Wearable devices can be configured to be coupled to a mobile device or external computer. The wearable device can include a wireless connection to the mobile device. The wearable device can include a sensor that is configured to measure motion of the user.

BRIEF DESCRIPTION OF THE DRAWINGS

The foregoing summary, as well as the following detailed description, will be better understood when read in conjunction with the appended drawings. For the purpose of illustration, there is shown in the drawings certain examples of the present disclosure. It should be understood, however, that the present inventive concept is not limited to the precise examples and features shown. The accompanying drawings, which are incorporated in and constitute a part of this specification, illustrate an implementation of apparatuses consistent with the present inventive concept and, together with the description, serve to explain advantages and principles consistent with the present inventive concept.

FIG. 4 shows an exemplary diagram of accelerometer data which has been processed by dynamic time warping.

DETAILED DESCRIPTION

Figure 1A:
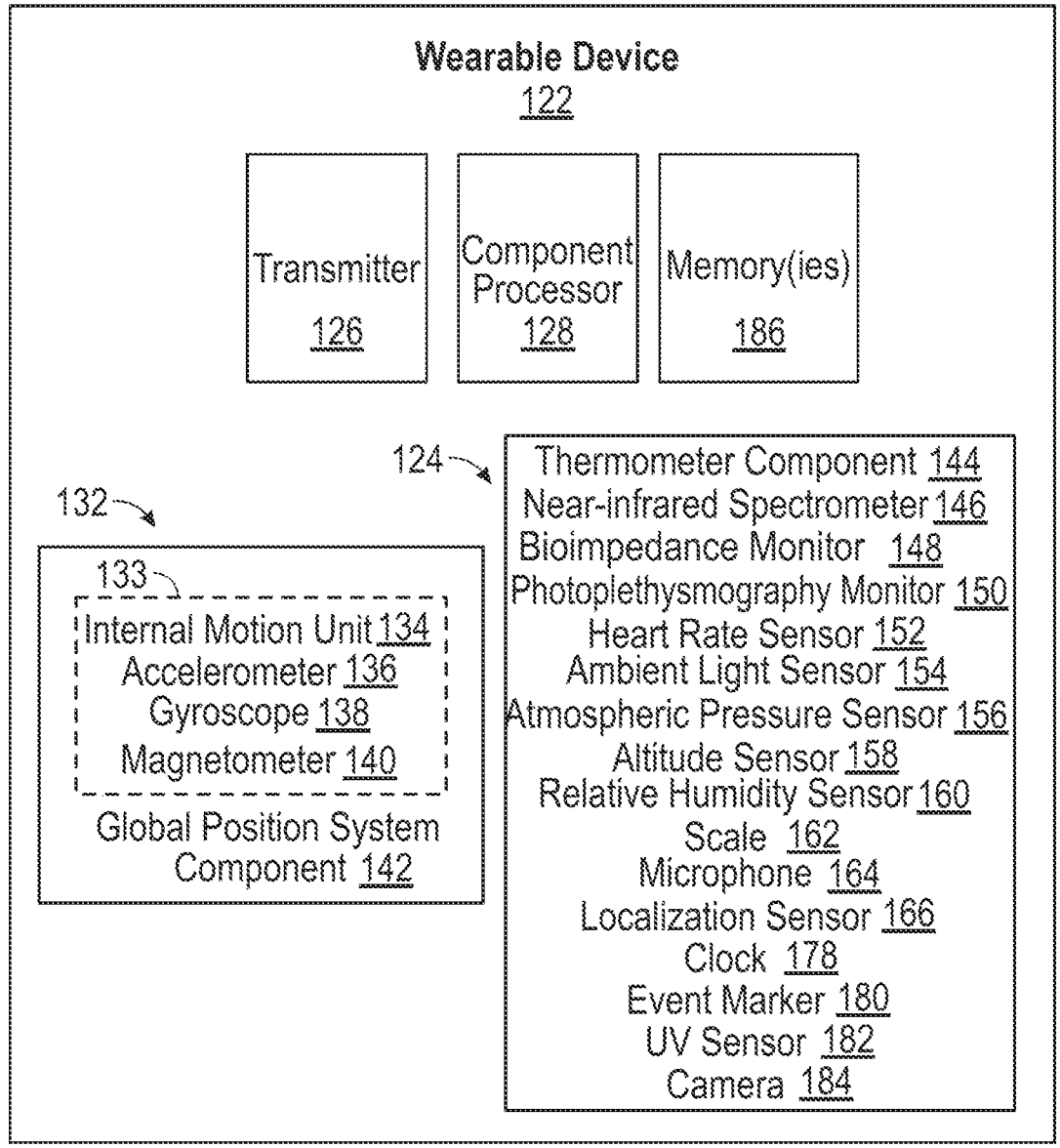
FIG. 1A illustrates an example of a wearable device according to the present disclosure.

Several definitions that apply throughout this disclosure will now be presented. The term "comprising" means "including, but not necessarily limited to"; it specifically indicates open-ended inclusion or membership in a so-described combination, group, series and the like. "About" refers to almost, nearly, on the verge of, or without significant deviation from the numeric representation. For example, about 20 can be 20, or a small deviation from 20. "Coupled" refers to the linking or connection of two objects. The coupling can be direct or indirect. An indirect coupling includes connecting two objects through one or more intermediary objects. Coupling can also refer to electrical or mechanical connections. Coupling can also include linking without physical contact. While "skin" is used throughout the disclosure, any suitable "tissue" of the user can be interchangeably used with "skin."

The present disclosure endeavors to solve a variety of problems in the industry. The present disclosure includes the ability to detect drink events. The present disclosure additionally includes the ability to estimate the volume of liquid ingested by a user during a drink event. The present disclosure also allows the monitoring of the hydration of a user.

The present disclosure includes a system and device for determining drink events using non-invasive techniques. Drink events include drinking fluids, such as water, soda, or any other fluid that the body intakes for hydration.

The present disclosure can be implemented in one or more of the devices and/or systems described herein. In one example, the present disclosure includes a wearable device. As used herein, a wearable device is any device that is in contact or close proximity to a user of the device. Examples of wearable devices include a wrist worn device, arm, hand and/or finger worn device, clothing, an athletic aid, a monitor, a bracelet, a band, a ring, and/or compression sleeves. The wearable devices can be configured to have a wireless communication or wired communication interface to allow for exchange of data. In at least one example, the wearable device is operable to be electronically coupled to a mobile device. In at least one example, the wearable device can be configured to include a user notification component that provides instructions to the user. The user notification component can be a display, an audio device, a vibration device, or a visual indicator. In other examples, the user notification component can be omitted and the wearable device can communicate instructions to the mobile device for communication of the instructions to the user.

The term mobile device can include a device that has a processor and a memory. The mobile device in at least some examples includes a display. Additionally, the mobile device can include a communication component that is operable to allow for communication with the mobile device to an external device. The wearable device can also be configured to communicate with one or more external sensor components. The wireless communication can be performed using short range wireless communication protocols such as BLUETOOTH, ZIGBEE, Advanced and Adaptive Network Technology (ANT+), WI-FI, Radio Frequency Identification (RFID), or the like.

Maintaining proper hydration is important not only to assure that athletes can maintain peak performance but also to maintain one's good health, cosmetic appearance, and wellness. Proper hydration is important to keep cognitive function and to help manage one's weight. It is also critical in maintaining one's good health, including preventing headaches, coronary heart disease, kidney stones, and cancer.

Hydration maintenance is best achieved under long-term and continuous monitoring of vital signs, rendering it a task that is best performed by a device that is in prolonged contact with the user, such as a wearable device. Moreover, wearable devices are capable of integrating a large range of sensors and a processor, storing the signals generated by these sensors in its internal memory for later processing and communicating these signals, or the results of its internal processing, to the user and to the world at large via wireless (or wired) communications, including storing data in the cloud for visualization, for further processing by a server, and/or for storage in a larger database, making aggregate data available to additional processing and/or to the development of new algorithms.

Maintaining proper hydration requires estimating the balance between fluid gains and fluid losses. That is to say, by monitoring drinks one can estimate the input side of hydration monitoring, resulting in the health and wellness benefits commonly associated with the maintenance of proper hydration.

In an example, a mobile device system includes a mobile device and a wearable device and is operable to detect drink events and/or monitor hydration for a user. The mobile device has at least one sensor which can detect motion of the mobile device. The wearable device can detect a biological indicator of the user and can transmit the data to the mobile device. The mobile device, or another component in the system, correlates the biological indicator of the user with the detected motion signal(s) in time to determine if one or more drink events has occurred and creates an input log for each drink event. In at least one example, the mobile device also determines a net balance of the user based on the input logs and output logs for expelled fluids by, for example, vomiting, urination, defecation, and/or perspiration. The net balance can provide the benefit of helping to improve the health and well-being of a user by being within a predetermined range, or below or above a predetermined threshold. For example, the net balance can be used to help a user to reach health-related goals such as, for example, staying well hydrated. To be well hydrated, a user should be above a hydration threshold. Although the system and device are described with respect to a mobile device, the system and device can be entirely operable on a wearable device.

In another example, a wearable device operable to detect drink events of a user includes at least one motion sensor operable to detect motion and record motion signals of the wearable device. The wearable device can further include a processor coupled to the at least one motion sensor and at least one biological sensor coupled to the processor and is operable to detect one or more biological indicators of the user. The wearable device can also include a memory that is operable to store instructions to cause the wearable device to do one or more of the following: obtain at least one biological indicator of the user, correlate the biological indicator of the user with the detected one or more motion signals, and determine that a drink event is detected based on the correlation between the detected motion signals and the at least one biological indicators.

In another example, a mobile device can be coupled with the wearable device and can include a processor. The mobile device can also include a display coupled to the processor and operable to display data received from the processor. The mobile device can also include a memory coupled to the processor and operable to store instructions to cause the processor to do one or more of the following: obtain, from the wearable device, at least one of the one or more biological indicators of the user, correlate the at least one biological indicators of the user with the detected one or more motion signals, and determine that a drink event is detected based on the correlation between the detected one or more motion signals and the at least one biological indicators.

FIG. 1A illustrates an example of a wearable device 122 according to the present disclosure. The wearable device 122 can include a transmitter 126, a component processor 128, one or more biological sensors 124, a memory 186, and one or more additional sensors 132. The wearable device 122 can include and/or be coupled with at least one external sensor component which can be one or more of: scales, water bottles, glucose measurement systems, blood pressure monitors, pulse oximeters, respiration rate monitors, tissue oximeters, respirators, electrocardiogram monitors, or the like. The wearable device 122 can also be enabled to wirelessly communicate with other devices.

The one or more biological sensors 124 can be coupled to the component processor 128 and is operable to detect a biological indicator 206 of a user 208. The transmitter 126 is operable to transmit a detected biological indicator 206 to the at least one communication component 118 of the mobile device 100, a remote computer 168, and/or another external device. The biological sensors 124 can include one or more of a thermometer component 144 operable to measure a temperature of skin of the user 208 and/or surrounding ambient temperature, a near-infrared spectrometer (NIRS) 146 operable to monitor chromophores that constitute a tissue of the user 208, a bioimpedance monitor 148, a photoplethysmography (PPG) monitor 150, a heart rate monitor 152, an ambient light sensor 154, an atmospheric pressure sensor 156, an altitude sensor 158, a relative humidity sensor 160, a scale 162, a microphone 164, a localization sensor 166, a clock 178, an event marker 180, a ultra violet (UV) sensor 182, and/or a camera 184. Furthermore, the one or more biological sensors can be operable to detect one or more biological indicators, which can include a heart rate, a heart rate variation, a blood pressure, a respiration rate, a blood oxygen saturation level, muscle oxygenation level, skin temperature, skin perfusion, skin impedance, galvanic skin response, blood pressure, tissue perfusion, blood flow, blood volume, extracellular fluid, tissue hydration, tissue hydration variation, intracellular fluid, photoplethysmograph, images, videos and/or sounds associated with a drink event. For example, the signals of a PPG monitor can be processed to measure blood oxygen saturation, heart rate, heart rate variation, blood pressure and/or respiration rate. As such, a PPG monitor may have the function of multiple individual sensors, and the device 122 can be more compact.

The additional sensors 132 include one or more motion sensors 133. The motion sensors 133 can include an inertial motion unit (IMU) 134, an accelerometer 136, gyroscope 138, and/or magnetometer 140. The additional sensors 132 can also include a global position system component 142 to assist in determining a physical location of the user.

Figure 1B:
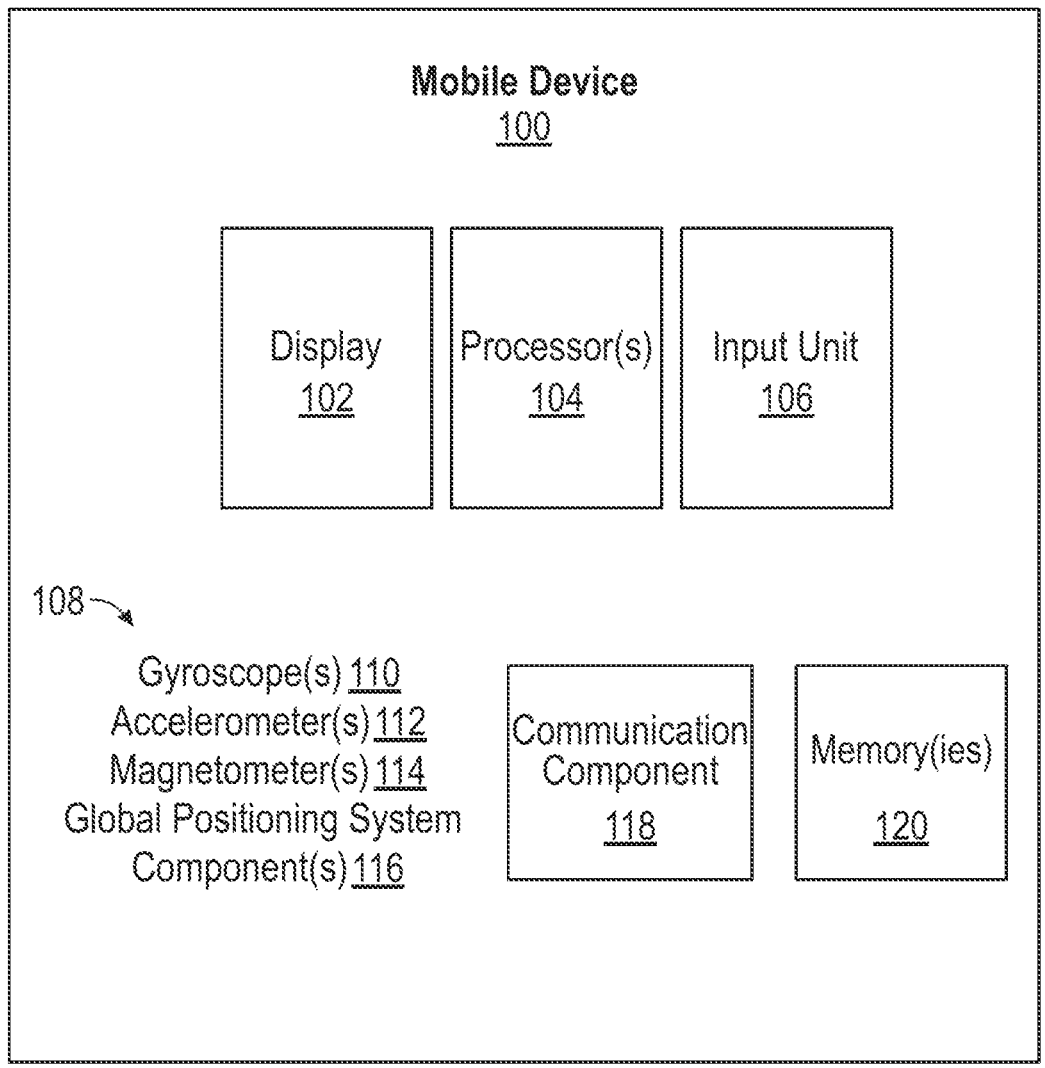
FIG. 1B illustrates an example of a mobile device according to the present disclosure.

FIG. 1B illustrates an example of a mobile device 100 according to the present disclosure. The mobile device 100 includes a display 102, a processor 104, an input unit 106, at least one sensor 108, at least one communication component 118, and a memory 120. The at least one sensor 108 is operable to detect motion of the mobile device 100. The at least one sensor 108 can be a gyroscope 110, an accelerometer 112, a magnetometer 114, and/or a global positioning system component 116. The at least one communication component 118 is operable to receive and/or transmit data from a wearable device 122 and/or a remote computer 168. The processor 104 is coupled to the at least one sensor 108 and the at least one communication component 118.

Figure 1C:
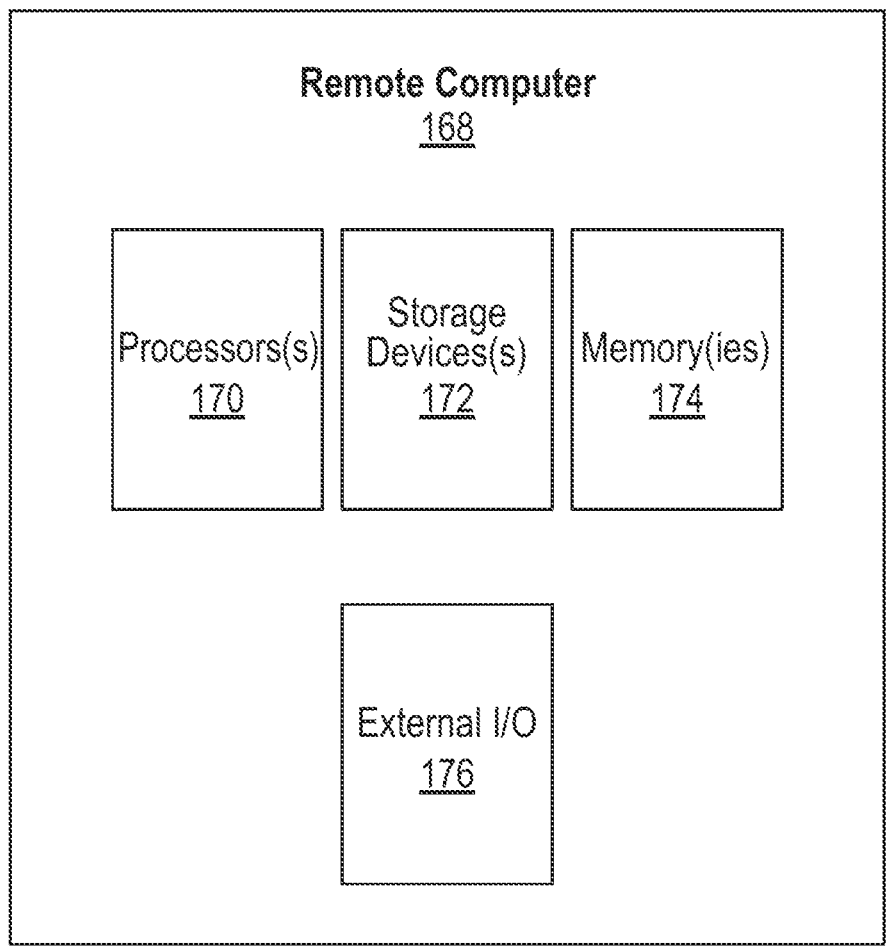
FIG. 1C illustrates an example of a remote computer according to the present disclosure.

FIG. 1C illustrates an example of a remote computer 168. The remote computer 168 can include one or more of: one or more processors 170, one or more storage devices 172, one or more memories 174, or one or more external Input/Output (IO) interfaces 176. The remote computer 168 can be a cloud based computer system 212, shown in FIG. 2 or a cloud storage and data processing system 105, shown in FIG. 1D.

Figure 1D:
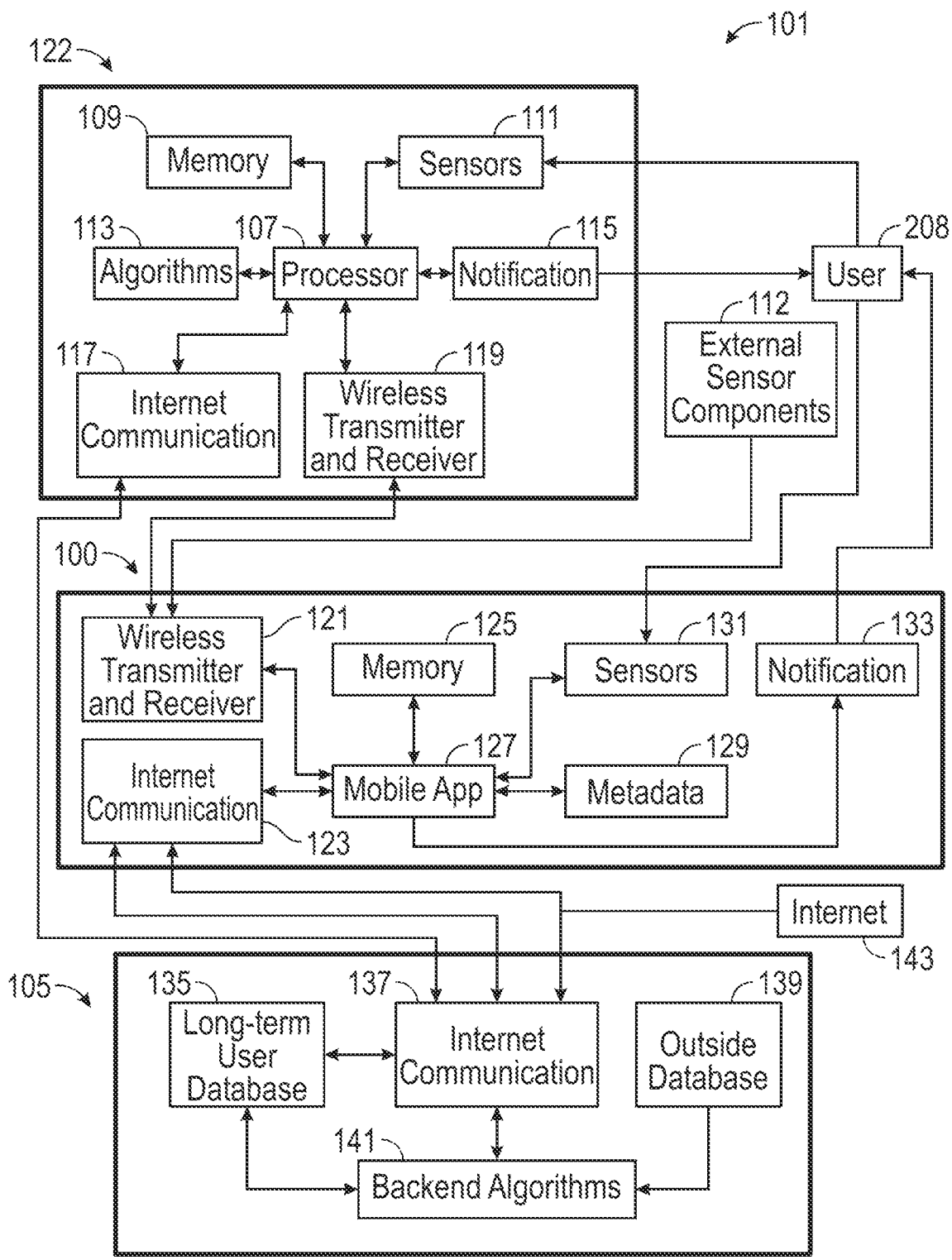
FIG. 1D is a schematic diagram of an example wearable device system according to the present disclosure.

FIG. 1D is a schematic diagram of an example wearable device system 101 according to the present disclosure. The wearable device system 101 can include the mobile device 100, the wearable device 122, and/or a cloud storage and data processing system 105. In at least one example, the cloud storage and data processing system 105 can include one or more of the components described in relation to the remote computer 168 of FIG. 1C. Further, an internet 143 is operable to allow communication between the mobile device 100, the wearable device 122, and/or the cloud storage and data processing system 105. The wearable device 122 can include one or more of: a processor 107 operable to communicate with a memory 109, one or more sensors 111, one or more algorithms 113, internet communication 117, and/or a wireless transmitter and receiver 119. In one example, the one or more sensors 111 collects data from a user 208 and the processor 107 processes the data and sends at least one notification 115 to the user 208. The at least one notification 115 can be provided to the user 208 via one or more of a display, lights, sound, vibrations, and/or buzzers. The at least one notifications 115 can further be associated with achieving one or more predefined goals, wherein the one or more predefined goals are health or well-being. In one example, the predefined goal can be to improve wellbeing by maintaining a level of hydration in order to increase a user's overall health. In another example, the predefined goal can be to stay hydrated within an allowable range of net hydration balance, thus preventing disease states related to dehydration. In other examples the predefined goal can include one or more goals, which can be both diet and exercise related. In other examples, the predefined goals can include skin beauty and/or mental alertness goals. In other examples, the predefined goals can include athletic performance goals, such as pre-hydrating in preparation for a given athletic event.

The mobile device 100 includes a mobile application 127 operable to communicate with one or more of a memory 125, a wireless transmitter and receiver 121, a metadata 129, a one or more sensors 131, and an internet communication 123. In an example, the mobile device 100 is controlled by the mobile application 127 that collects additional data from the one or more sensors 131 and also collects the metadata 129. The metadata 129 can be, for example, from one or more of a user's calendar, contacts, or geographic location.

The cloud storage and data processing system 105 can include one or more backend algorithms 141 operable to communicate with a long-term user database 135, one or more outside databases 139, or an interne communication 137. The cloud storage and data processing system 105 enables the storage of long-term user data into the long-term user database 135 and the execution of more complex backend algorithms 141. These backend algorithms 141 also benefit from the long-term data derived from other users that are similar to a specific user. The information derived from the backend algorithms 141 are provided to the user 208 either via the mobile application 127 or directly to the wearable device 122.

Figure 2:
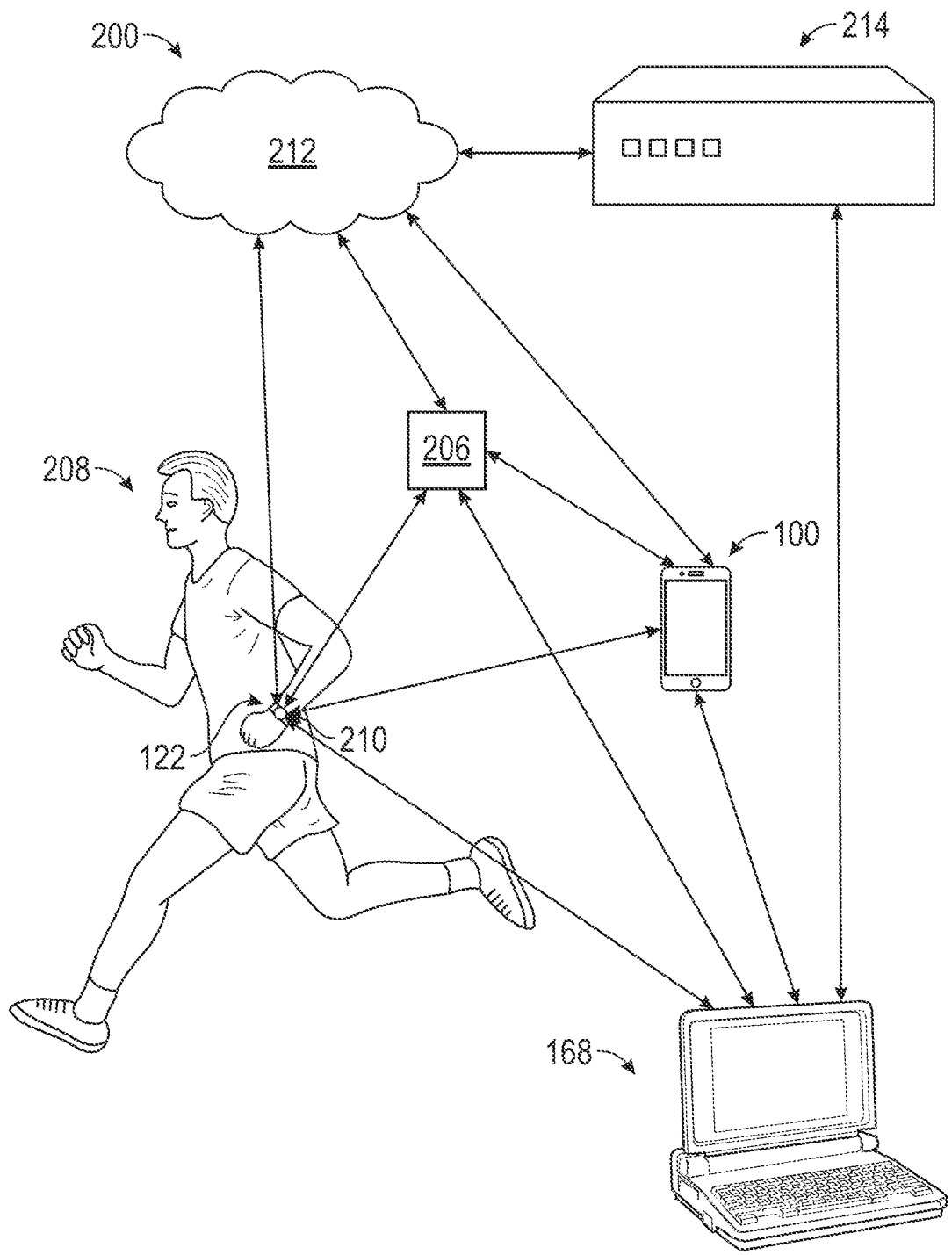
FIG. 2 is a schematic diagram of an example mobile device system according to the present disclosure.

FIG. 2 illustrates an example mobile device system 200. The mobile device system 200 can include a mobile device 100, one or more wearable devices 122, a remote computer 168, a cloud-based computer system 212, and/or a storage device 214. The components can communicate with each other as indicated by the arrows shown. For example, the mobile device 100 can communicate with one or more of the cloud based computer system 212, the remote computer 168, or the one or more wearable devices 122.

In one example according to the present disclosure, the one or more wearable devices 122 can be in the form of a wrist device 210 operable to be worn on a wrist of a user 208. The wrist device 210 can also include additional sensors 132 (shown in FIG. 1A) to measure motion of a wrist and record motion signals corresponding to the measured motion.

The motion sensors 133 provide the wearable device 122 with a set of motion signals indicative of the position or motion of the limb in which the wearable device 122 is worn—typically the wrist. The motion signals are then processed, for example, either by the IMU and/or by the processor, to generate a new signal indicative of significant motion. For example, the motion signal can be the sum of the squares of the accelerations measured in the x, y and z axes of the accelerometer present in the IMU. Once the motion signal is detected above a certain threshold level (for example, at least 1.5 times higher than the level of motion detected when the user is at rest) the wearable device 122 processes the other signals, for example additional x, y, and z accelerations, provided by the motion sensors 133 in order to identify the motion being undertaken by the user.

Drinking motions often consists of the user moving his/her dominant arm toward their mouths. To prevent confusing drinking motions with other similar motions a library of motions can be created by having a number of users perform similar motions in a large number of trials. The motions are labeled and identified as to what motions they represent at a given point in time and with a given duration. As such, machine learning classification algorithms, such as k-nearest neighbors, support vector machines, decision tress, time-delay neural networks, linear and quadratic discriminant analysis, can be used to distinguish between true drinking motions from other (false-positive) motions. The resulting classifier algorithms and their pertinent parameters can be loaded onto the wearable device memory 186 and the algorithm is executed by the processor 128 whenever a significant motion is detected, resulting in a new signal indicative of a drinking motion.

Figure 3A:
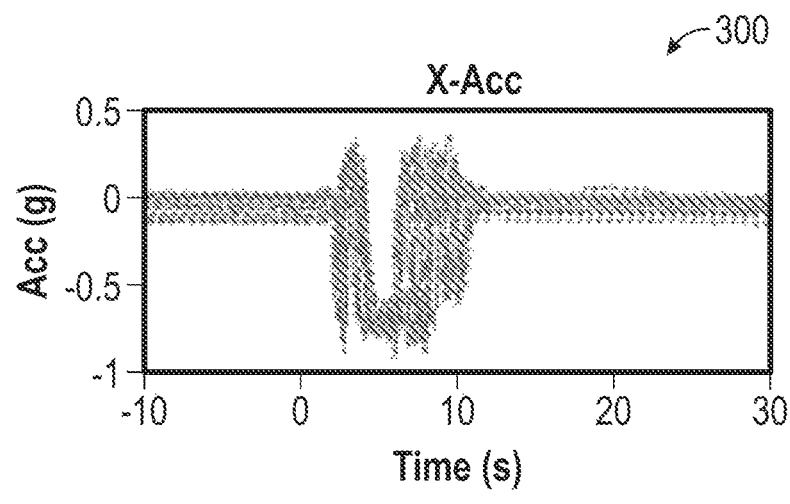
FIG. 3A illustrates exemplary accelerometer data used to detect matter input from the x axis of the accelerometer.
Figure 3B:
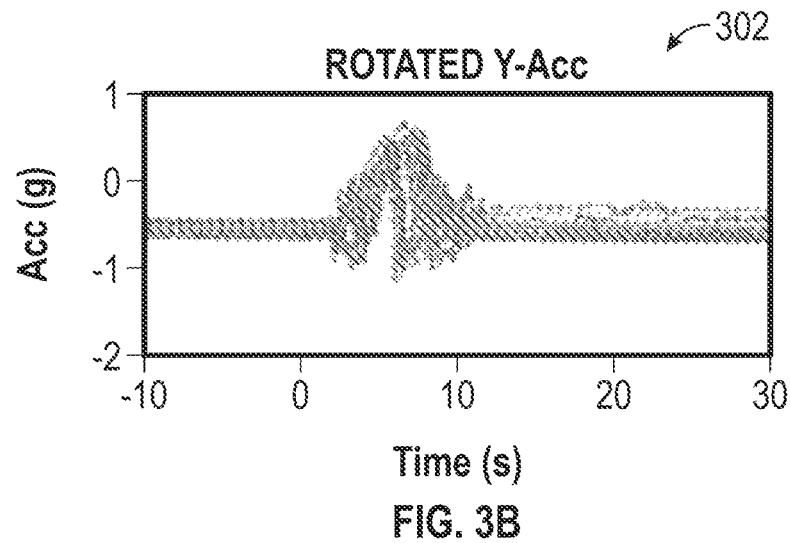
FIG. 3B illustrates exemplary accelerometer data used to detect matter input from the y axis of the accelerometer.
Figure 3C:
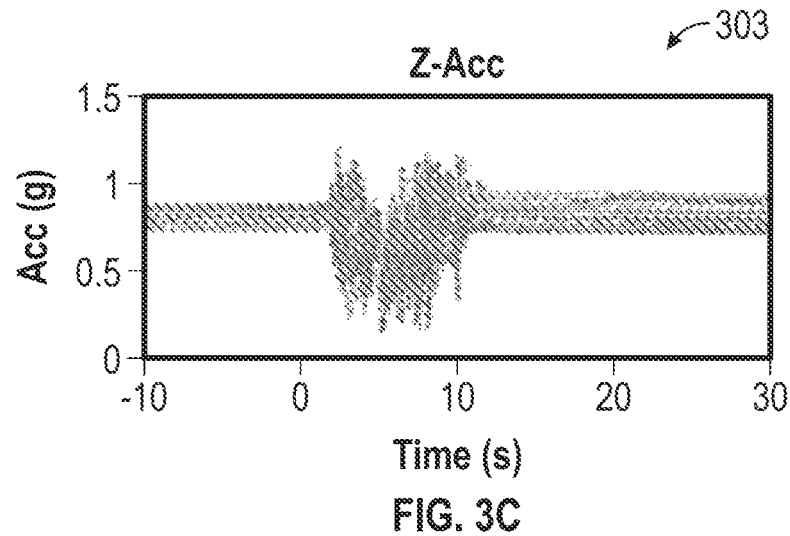
FIG. 3C illustrates exemplary accelerometer data used to detect matter input from the z axis of the accelerometer.

For example, as shown in FIGS. 3A-3C, the three plots 300, 302, 303 depict the x, y, and z axis of accelerometers, demonstrating that accelerometer data can be used to detect drink events. In the example shown in FIGS. 3A-3C, the acceleration of the wrist of three different subjects was monitored while the subjects ingested twenty different boluses of an electrolyte solution with volumes varying from 0.5 to 4 oz each, showing a high degree of repeatability from drink motion to drink motion, thus demonstrating that drink motions can be effectively identified using accelerations measured by a wrist-worn motion sensors 133.

In at least one example, the velocity with which the user's hands move during drinking events can vary considerably from person-to-person and even within the same person. To ensure that drinking motions are represented in a similar way under most conditions, the acceleration data can be segmented and pre-processed using techniques such as dynamic time warping, dynamic tiling, and fast Fourier transforms after zero padding. FIG. 4 shows an example of dynamic time warping for mapping an input signal 402 into another temporal signal 404 by matching features that are common in both versions of the signal as depicted by dashed lines 406. This common mapping allows the direct comparison of the transformed signal with other signals available in a signal library representative of drinking motions.

Moreover, the motion signals can be processed using adaptive algorithms that are sensitive to temporal variations, such as time-delay or finite impulse response (FIR) neural networks, and/or long short term memory networks (LSTMN). Every time a user newly dons a wearable device, the wearable device 122 may be located in a slightly different location. Similarly, different users may drink in slightly different ways. Thus, adaptive signal processing methods can be employed to adjust for user-to-user and wear-to-wear variations. For example, a rotation matrix can be used to re-orient the wearable device 122 regardless of the orientation in which the wearable device 122 is worn.

The drink and non-drink class of activities can also be distinguished using algorithms such as Normal Activity Recognition, Activity Thresholds, and k-nearest neighbors. In Normal Activity Recognition, for example, specific activities can be recognized by first computing the surface normal and then comparing the temporal variation of the surface normal vector against those of pre-trained activities stored in a local library. In the k-nearest neighbors classification method, an input sample point can be assigned the category label of the k nearest set of previously classified points. For example, using a nearest-neighbor algorithm, drinking events can be distinguished from non-drinking events with an accuracy better than 92%, a sensitivity better than 89% and a specificity better than 87%.

To determine that a drink event occurred with greater accuracy, the wearable device 122 can correlate biological indicators from biological sensors 124 along with the motion signals from the motion sensors 133. For example, a user stops breathing in order to take a drink. As such, the biological indicator may include a breathing rate, or pauses in breathing. Additionally, to compensate for the momentary loss in arterial blood oxygenation due to the user stopping breathing, the user's circulatory system increases oxygen delivery by increasing the blood flow and by increasing the heart rate. As such, the heart rate variability (HRV) also increases while the user respiration rate suffers a decrease. Therefore, the biological indicator may include a surge in heart rate and/or changes in HRV.

Drinking may not be the only action that causes a change in heart rate over a period of time. The period of time may be, for example, 3 seconds, 10 seconds, or 30 seconds. Changes in heart rate can also be caused by other actions that require compensation through a change in blood volume. For example, when a person stands up suddenly their heart rate usually increases to assure proper oxygenation to their head at a higher elevation. As such, the wearable device 122 may utilize additional biological indicators indicative of a drink event. For example, the thermometer component 144 may provide biological indicators that can include changes in skin and/or core temperatures, changes in skin and/or core temperatures with respect to ambient temperature as drinks tend to be at a different temperature compared to ambient temperature. For example, drinks tend to be cold when the ambient temperature is hot and vice-versa. Another biological indicator can be an increase in skin perfusion. The skin typically works as a water reservoir. As such, when a user dehydrates, their peripheral vasculature may constrict, leading to reduced perfusion in the skin and extremities. Conversely, when a user drinks and rehydrates, perfusion may increase. As such, a near-infrared spectrometer 146 can measure tissue hydration and/or tissue perfusion, and the wearable device 122 can determine that a drink event is detected when an increase in tissue perfusion is measured. Other examples of biological indicators that can be used to detect drink events include the sounds and images associated with drinking, which can be captured by microphones, still and video cameras embedded on the wearable device 122 and/or the mobile device 100.

Drinking also can increase the amount of blood plasma and the balance between intracellular and extracellular fluids, and that change in ratio, such as tissue hydration variation, can be measured using bioimpedance monitors 148. During water absorption events, water is typically first ingested luminally before being absorbed by the digestive tract, at which point the water is transferred into the blood plasma. From the blood plasma, water is distributed throughout the body to arterioles and capillaries, where water becomes extracellular fluid before being osmotically absorbed by the cells in the body, thus becoming intracellular fluid. Cell membranes contain fatty tissue and are thus highly resistant to electric current while fluid is highly conductive. Thus, measuring the bioimpedance of the body provides one with an estimate of the ratio of intracellular over extracellular fluid content, thereby providing us with an estimate of fluid flow within the user body. The bioimpedance monitors 148 may measure biological indicators including galvanic skin response, skin resistance, skin conductance, electrodermal response, psychogalvanic reflex, skin conductance response, sympathetic skin response, skin conductance level, and/or electrodermal activity.

Figure 5:
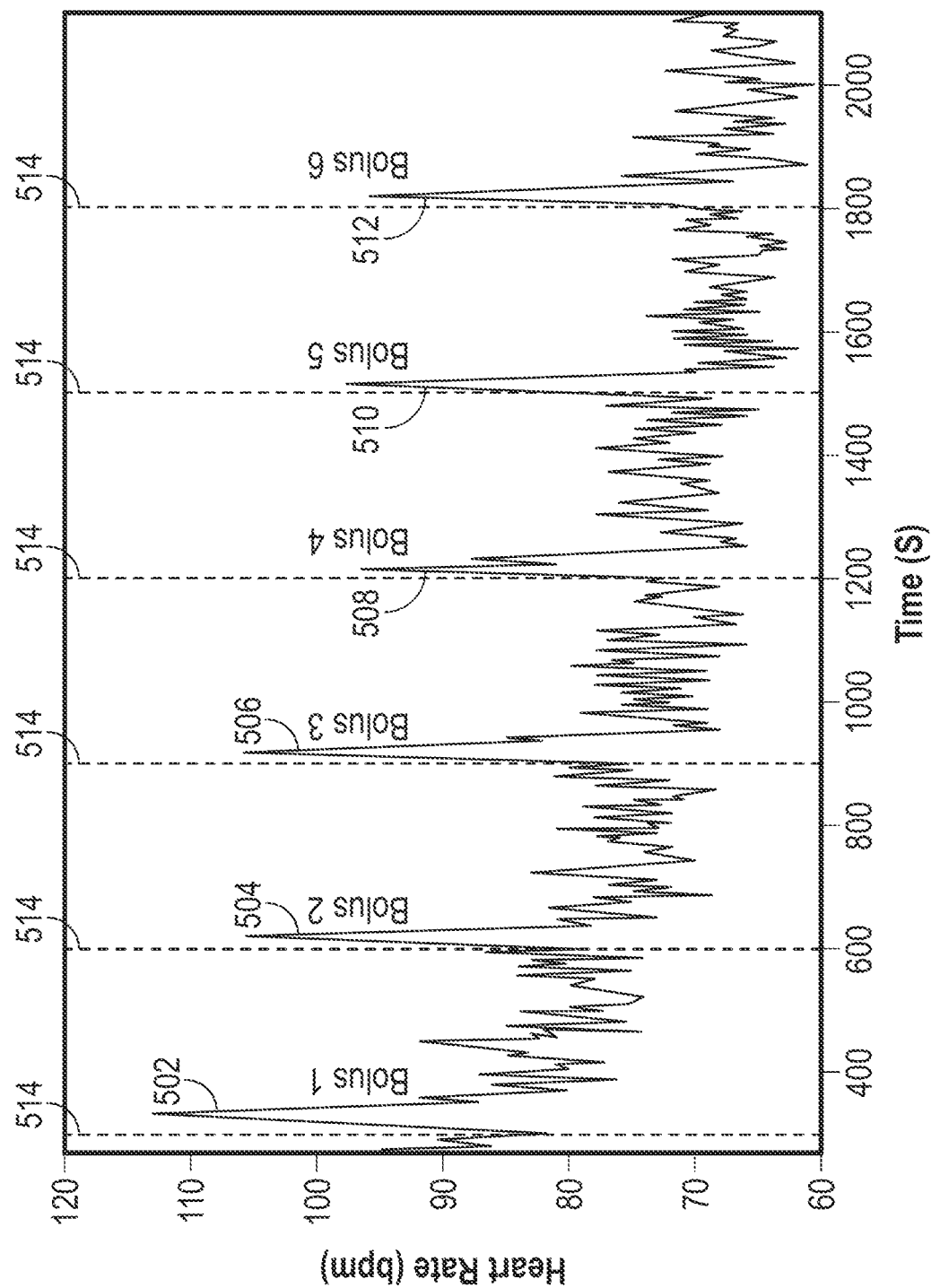
FIG. 5 shows an example using heart rate to detect a drink event.

FIG. 5 shows an example of a biological signal used to indicate the time and volume of a drink event. In the example shown in FIG. 5, the heart rate of a user was monitored using a heart rate sensor 152 while the user ingested six boluses of an electrolyte solution: 250 ml in the first bolus 502 and 153 ml in each of the subsequent five boluses 504, 506, 508, 510, 512, corresponding to a total of 14 ml per kg of total body mass. The dashed lines 514 mark the beginning of each one of the drink events. The user's heart rate surges shortly after each drink and the surge in hear rate lasts approximately the duration of the drinking event. Therefore, during a drink event both the amplitude and duration of the heart rate surge (above baseline) increase as a function of the volume of fluid ingested. In at least one example, the volume of ingested fluid can be estimated by the area-under-the-curve between the surge and baseline signals.

Additionally, to improve the detection of drink events, the wearable device 122 and/or the mobile device 100 can access specific events on the user's calendar and/or social media accounts to aid in the determination of whether or not the user is undergoing a drink event at a given time. For example, references to words such as "Lunch," "Dinner," and "Breakfast" are associated with a higher probability of drinking while words such as "Run," "Workout," and "Spin class" are more closely associated with output events that lead to a loss of hydration volume due to increased physical activity, resulting in a higher loss of liquids due to increased perspiration and respiration rate. The wearable device 122 and/or the mobile device 100 may also use one or more of the user's contacts and/or calendar events to determine whether the user is in a location and/or the presence of one or more people with whom the user experiences drink events.

Additionally, the wearable device 122 and/or the mobile device 100 may use the user's physical location to assist in the estimate of whether the user is likely to undergo an input or output event. For example, the probability of the user drinking is higher when the user is in a restaurant, bar, cafe, or cafeteria. Indicators of physical location can also include ambient light and UV exposure detectors measured, for example, by ambient light sensors 154, indicating whether the user is indoors or outdoors. Additional examples of physical location indicators can include knowledge of previous locations regularly visited by the user and stored in memory 186, the use of altitude sensors 158, atmospheric pressure sensors 156, and relative humidity sensors 160 detectors to determine whether the user is indoors or outdoors and/or at what floor of a given building, and captured images and/or videos by camera 184. The wearable device 122 and/or the mobile device 100 can also send one or more notifications 133 to the user 208. The notifications 133 can also be provided to the user 208 via one or more of a display, lights, sound, vibrations, and/or buzzers.

In at least one example, the detected motion signals then can be transmitted to the mobile device 100 or remote computer 168. The wrist device 210 can also be operable to communicate with the mobile device 100 or other connected device via a wired or wireless communication connection. For example, the wrist device 210 can wirelessly communicate with the mobile device 100, the remote computer 168, or a cloud based computer system 212 indicated by the arrows shown in FIG. 2. In another example, the wrist device 210 can communicate with the mobile device 100, the remote computer 168, or the cloud based computer system 212 via a wired connection. The wrist device 210 can be entirely self-sufficient. In other examples, the wrist device 210 can be without a connection to the internet and/or mobile device 100. The data transmitted to the cloud based computer system 212 or other long-term memory storage device can be stored for future use and/or processed to provide information useful to a user 208.

The memory 120 of the mobile device 100 can be operable to store further instructions to cause the mobile device 100 to display a recommendation to the user 208 for a next drink event that includes an input activity, an input timing, and/or an input duration. In at least one example, the wearable device 122 can display the information without the presence of the mobile device 100. For example, the mobile device 100 or wearable device 122 can display instructions to drink two ounces of water in about five minutes while a user 208 is running. Furthermore, the memory 120 of the mobile device 100 can cause the mobile device 100 to display a determined drink event on a display of the mobile device and receive confirmation or modification of the displayed drink event. Also, the display 102 can display data received from the remote computer 168, the cloud based computer system 212, and/or the one or more wearable devices 122.

The display 102 can also display an output event that includes one or more of: an output activity, an output timing, and/or an output duration. The output events can be perspiration, urination, defecation, excretion, coughing, sneezing, vomiting, blood loss, plasma loss, ascetic fluid loss, fluid redistribution, diarrhea, temperature loss, temperature change, insensible fluid loss, fat loss, muscle loss, bone loss, calories burnt, sleep loss, attention loss, alertness loss, or yelling or crying (indicators of mood loss or the like).

Furthermore, the net balance of input and/or output can be displayed. The long-term monitoring of the net balance of input events and output events can be used by the mobile device 100 and/or wearable device 122 to provide the user 208 with relevant information regarding their health, wellness, and cosmetic appearance. The beneficial information includes hydration balance. For example, the mobile device 100 and/or the wearable device 122 can use sensed estimates of drink events and fluid intake to notify the user to continue drinking fluid.

Figure 6:
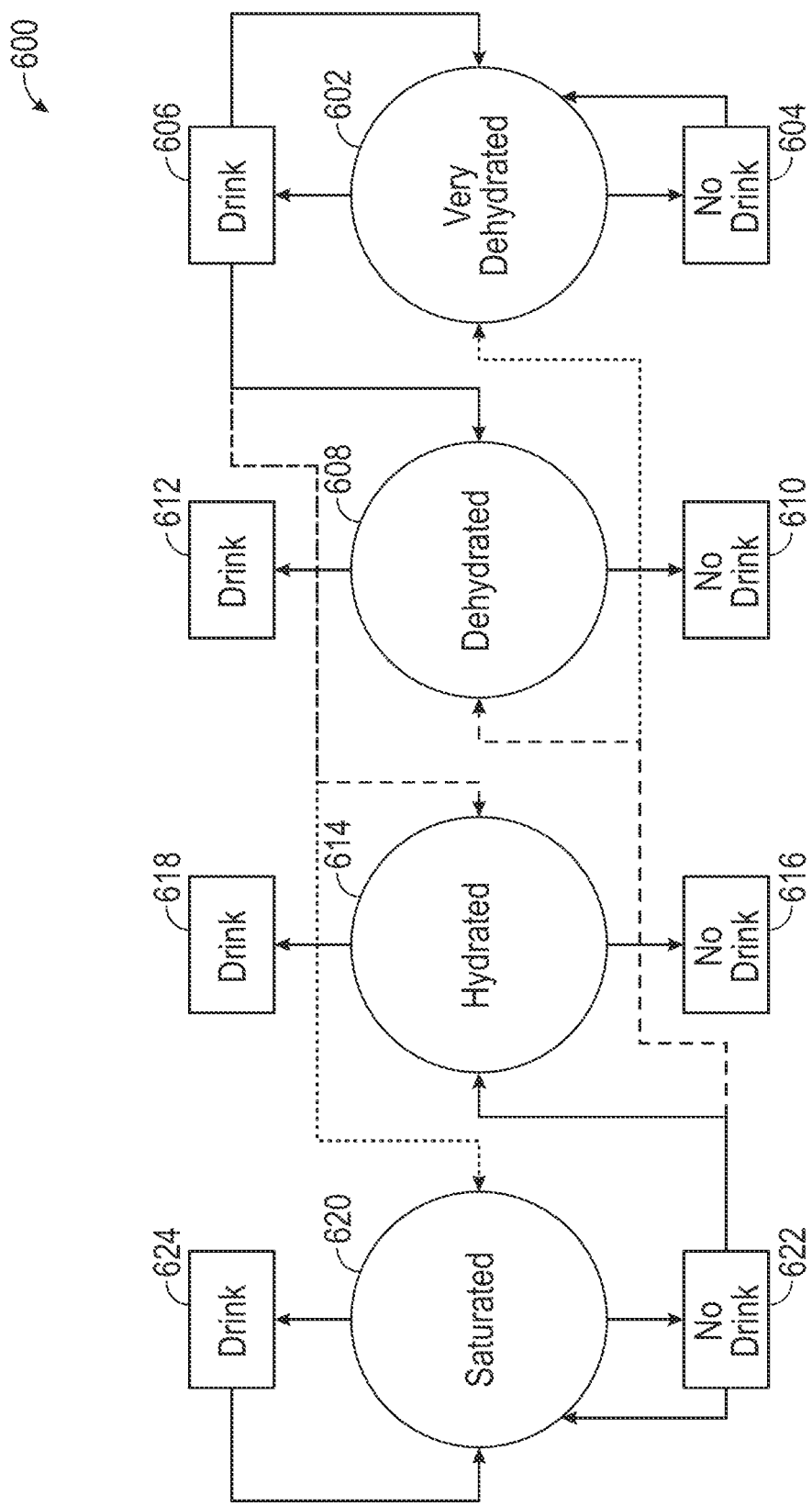
FIG. 6 shows a diagram of drink events corresponding to hydration status.

As shown in FIG. 6, an example of how drink detection events can be used to help determine the hydration status of a user. The diagram 600 shown in FIG. 6 depicts a Markov decision process, where the present state is independent of past states. Methods for solving Markov decision processes include dynamic Bayesian networks and maximum likelihood estimators. Expectation-maximization algorithms, such as the Baldi-Chauvin algorithm and the Markov-chain Monte Carlo algorithm, can also be included, as well as on-line learning algorithms such as the Baum-Welch algorithm, the Bayesian online algorithm and the Mean Posterior approximation algorithm. Also, the current state of the user may not be known a priori and only inferred from observations of their actions, which is called a "hidden Markov model" and can also be solved by the algorithms listed above, with or without modifications.

In the example diagram 600 shown in FIG. 6, a set of possible user states include saturated 620, hydrated 614, dehydrated 608, and very dehydrated 602 which are represented by circles. Each user state may correlate to a range of hydration levels. For each user state, there are sets of two possible user actions such as drink 624, 618, 612, 606 and no drink 622, 616, 610, 604 which are represented by rectangles. Arrows show possible future states once a user has undertaken a given action, with solid arrows representing transition probabilities that are higher than those of dashed arrows, which are higher than those represented by dotted arrows. For example, when the user state is very dehydrated 602, the user can not drink 604, and the probability of the user being very dehydrated 602 is high. The user can also drink 606, and the probability of the user transitioning to dehydrated 608 or remaining very dehydrated 602 are high. The probability of the user transitioning to hydrated 614 is medium, and the probability of the user transitioning to saturated is low. Note that for exemplary purposes, only the transition probability arrows associated with the Drink action 606 and No Drink action 604 associated with the Very Dehydrated state 602, and the transition probability arrows associated with the Drink action 624 and No Drink action 622 associated with the Saturated state 620 are shown. All other transition probability arrows associated with all actions, all states, do exist but are omitted from diagram 600 for clarity.

The use of at least one sensor 108 or biological sensors 124 can be used in isolation or in combination. For example, the mobile device 100 can obtain data from the IMU 134, wherein the determination of one or more drink events is based on the obtained data from the IMU 134 with respect to time and/or heart rate. In at least one example, the time of a heart rate spike and motion detected from the IMU 134 can indicate the start of a drink event. Furthermore, predetermined motions, such as a return to a position prior to initiation of the input event, for example, can indicate an end of a drink event.

In at least one example according to the present disclosure, a mobile device 100 is operable to determine habits of a user 208 and to make recommendations regarding changes in habits. The mobile device 100 includes one or more internal sensors 108 operable to detect at least one of a motion of the mobile device 100 or location of the device. The mobile device 100 also includes a processor 104 coupled to the one or more internal sensors 108 and a display 102 coupled to the processor 104 and operable to display data 314 received from the processor 104. The communication component 118 is coupled to the processor 104 and is operable to receive data 314 from at least one of: a remote computer 168 or one or more external sensor components 122 operable to detect a biological indicator 206. The mobile device 100 further includes a memory 120 coupled to the processor 104 and is operable to store instructions to cause the processor to perform the process of logging input events. In at least one example, the wearable device 122 is operable to determine habits of a user 208 and make recommendations 320 regarding changes in habits without the use of a mobile device 100 and/or a remote computer 168.

In at least one example according to the present disclosure, a mobile device system 200 is operable to provide recommendations on input for a user 208 including one or more of: a mobile device 100 and an external sensor 122. The mobile device 100 includes at least one sensor 108 operable to detect motion of the mobile device 100 and at least one communication component 118 operable to receive data 314 from one or more external sensor components 122 or remote computer 168. The mobile device 100 also includes a processor 104 coupled to the at least one sensor 108 and the at least one communication component 118. The mobile device system 200 also can include one or more of: an external sensor component 122 having a component processor 128; a biological sensor 124 coupled to the component processor 128 and operable to detect a biological indicator 206 of the user 208; or a transmitter 126 operable to transmit the detected biological indicator 206 to the at least one communication component 118 of the mobile device 100. The remote computer 168 includes a processor 170 and a memory 174 that is operable to store instructions to perform the process of logging input events.

Numerous examples are provided herein to enhance understanding of the present disclosure. A specific set of statements are provided as follows.

Statement 1: A wearable device is disclosed comprising: at least one motion sensor operable to detect one or more motion signals; a processor coupled to the at least one motion sensor; one or more biological sensors coupled to the processor and operable to detect one or more biological indicators of a user; and a memory configured to store instructions executable by the processor, the instructions, when executed, are operable to: obtain, from the at least one motion sensor, at least one of the one or more motion signals; obtain, from the one or more biological sensors, at least one of the one or more biological indicators of the user; correlate the at least one biological indicators of the user with the detected one or more motion signals; and determine that a drink event is detected based on the correlation between the detected one or more motion signals and the at least one biological indicators.

Statement 2: A wearable device is disclosed according to Statement 1, wherein the one or more motion signals is pre-processed using dynamic time warping.

Statement 3: A wearable device is disclosed according to Statements 1 or 2, wherein the at least one motion sensor includes an inertial motion unit, an accelerometer, a magnetometer, and/or a gyroscope.

Statement 4: A wearable device is disclosed according to any of preceding Statements 1-3, wherein the one or more motion signals is processed by a machine learning classification technique.

Statement 5: A wearable device is disclosed according to Statement 4, wherein the machine learning classification technique includes k-nearest neighbor classifier and/or a neural network classifier.

Statement 6: A wearable device is disclosed according to any of preceding Statements 1-5, wherein the one or more biological sensors includes a heart rate sensor, and the one or more biological indicators includes a heart rate and/or a heart rate variation.

Statement 7: A wearable device is disclosed according to any of preceding Statements 1-6, wherein the one or more biological indicators includes a surge in the heart rate.

Statement 8: A wearable device is disclosed according to any of preceding Statements 1-7, wherein the one or more biological sensors includes a thermometer, and the one or more biological indicators includes tissue temperature and ambient temperature.

Statement 9: A wearable device is disclosed according to Statement 8, wherein the one or more biological indicators includes a decrease in tissue temperature and/or a decrease in tissue temperature with respect to the ambient temperature.

Statement 10: A wearable device is disclosed according to any of preceding Statements 1-9, wherein the one or more biological sensors includes a respiration detector, and the one or more biological indicators includes a pause in breathing.

Statement 11: A wearable device is disclosed according to any of preceding Statements 1-10, wherein the one or more biological sensors includes a near-infrared spectrometer, and the one or more biological indicators include an increase in tissue perfusion and/or blood volume.

Statement 12: A wearable device is disclosed according to any of preceding Statements 1-11, wherein the one or more biological sensors includes a photoplethysmography monitor, and the one or more biological indicators includes a blood oxygen saturation, a heart rate, a heart rate variation, a blood pressure, and/or a respiration rate.

Statement 13: A wearable device is disclosed according to any of preceding Statements 1-12, wherein the one or more biological sensors includes a bioimpedance monitor, and the one or more biological indicators includes tissue hydration variation.

Statement 14: A wearable device is disclosed according to any of preceding Statements 1-13, wherein the one or more biological sensors includes an atmospheric pressure sensor, an altitude sensor, a relative humidity sensor, a microphone, a clock, and event marker, and/or a camera.

Statement 15: A wearable device is disclosed according to Statement 13, wherein the one or more biological indicators includes an increase in blood volume, blood pressure, atmospheric pressure, altitude, humidity, sounds associated with eating and/or drinking, time, span of time, images and/or videos associated with drinking.

Statement 16: A wearable device is disclosed according to any of preceding Statements 1-15, further comprising: one or more additional sensors coupled to the processor and operable to detect one or more additional indicators, and the instructions are further operable to: obtain, from the one or more additional sensors, at least one of the one or more additional indicators; correlate the at least one additional indicator with the at least one biological indicators of the user and the one or more motion signals; determine that the drink event is detected based on the correlation between the at least one additional indicator and the one or more motion signals and the at least one biological indicators.

Statement 17: A wearable device is disclosed according to Statement 16, wherein the one or more additional sensors includes a global position system component, and the one or more additional indicators includes a physical location.

Statement 18: A wearable device is disclosed according to Statement 17, wherein the physical location includes a restaurant and/or a bar.

Statement 19: A wearable device is disclosed according to Statements 17 or 18, wherein the physical location is determined by a calendar, events and/or postings on one or more social media applications, ambient light, UV exposure, humidity, altitude, images, videos, and/or previously visited locations.

Statement 20: A system is disclosed comprising: a wearable device including: at least one motion sensor operable to detect one or more motion signals; a processor coupled to the at least one motion sensor; one or more biological sensors coupled to the processor and operable to detect one or more biological indicators of a user; and a mobile device communicatively coupled with the wearable device, the mobile device including a memory configured to store instructions executable by the processor, the instructions, when executed, are operable to: obtain, from the wearable device, at least one of the one or more motion signals; obtain, from the wearable device, at least one of the one or more biological indicators of the user; correlate the at least one biological indicators of the user with the one or more motion signals; and determine that a drink event is detected based on the correlation between the one or more motion signals and the at least one biological indicators.

Statement 21: A system is disclosed according to Statement 20, wherein the one or more motion signals is preprocessed using dynamic time warping.

Statement 22: A system is disclosed according to Statements 20 or 21, wherein the at least one motion sensor includes an inertial motion unit, an accelerometer, a magnetometer, and/or a gyroscope.

Statement 23: A system is disclosed according to any of preceding Statements 20-22, wherein the one or more motion signals is processed by a machine learning classification technique.

Statement 24: A system is disclosed according to Statement 23, wherein the machine learning classification technique includes k-nearest neighbor classifier and/or a neural network classifier.

Statement 25: A system is disclosed according to any of preceding Statements 20-24, wherein the mobile device further includes a global position system component operable to determine a physical location of a user; the instructions, when executed, are further operable to: correlate the physical location of the user with the at least one biological indicators and the one or more motion signals; and determine that a drink event is detected based on the correlation between the physical location and the at least one biological indicators and the one or more motion signals.

Statement 26: A system is disclosed according to any of preceding Statements 20-25, wherein the one or more biological sensors includes a heart rate sensor, and the one or more biological indicators includes a heart rate and/or a heart rate variation.

Statement 27: A system is disclosed according to Statement 26, wherein the one or more biological indicators includes a surge in the heart rate.

Statement 28: A system is disclosed according to any of preceding Statements 20-27, wherein the one or more biological sensors includes a thermometer, and the one or more biological indicators includes tissue temperature and ambient temperature.

Statement 29: A system is disclosed according to Statement 28, wherein the one or more biological indicators includes a decrease in tissue temperature and/or a decrease in tissue temperature with respect to the ambient temperature.

Statement 30: A system is disclosed according to any of preceding Statements 20-29, wherein the one or more biological sensors includes a respiration detector, and the one or more biological indicators includes a pause in breathing.

Statement 31: A system is disclosed according to any of preceding Statements 20-30, wherein the one or more biological sensors includes a near-infrared spectrometer, and the one or more biological indicators includes an increase in tissue perfusion and/or blood volume.

Statement 32: A system is disclosed according to any of preceding Statements 20-31, wherein the one or more biological sensors includes a photoplethysmography monitor, and the one or more biological indicators includes a blood oxygen saturation, a heart rate, a heart rate variation, a blood pressure, and/or a respiration rate.

Statement 33: A system is disclosed according to any of preceding Statements 20-32, wherein the one or more biological sensors includes a bioimpedance monitor, and the one or more biological indicators includes tissue hydration variation.

Statement 34: A system is disclosed according to any of preceding Statements 20-33, wherein the one or more biological sensors includes an atmospheric pressure sensor, an altitude sensor, a relative humidity sensor, a microphone, a clock, an event marker, and/or a camera.

Statement 35: A system is disclosed according to Statement 34, wherein the one or more biological indicators includes an increase in blood volume, blood pressure, atmospheric pressure, altitude, humidity, sounds associated with eating and/or drinking, time, span of time, images and/or videos associated with drinking.

Statement 36: A system is disclosed according to any of preceding Statements 25-35, wherein the physical location is determined by a calendar, events and/or postings on one or more social media applications, ambient light, UV exposure, humidity, altitude, images, videos, and/or previously visited locations.

The description above includes example systems, methods, techniques, instruction sequences, and/or computer program products that embody techniques of the present disclosure. However, it is understood that the described disclosure can be practiced without these specific details.

It is believed that the present disclosure and many of its attendant advantages will be understood by the foregoing description, and it will be apparent that various changes can be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various examples, it will be understood that these examples are illustrative and that the scope of the disclosure is not limited to them. Many variations, modifications, additions, and improvements are possible. More generally, examples in accordance with the present disclosure have been described in the context of particular implementations. Functionality can be separated or combined in blocks differently in various examples of the disclosure or described with different terminology. These and other variations, modifications, additions, and improvements can fall within the scope of the disclosure as defined in the claims that follow.

What is claimed is:

1. A method comprising:
obtaining, from at least one motion sensor, one or more motion signals;
obtaining, from one or more biological sensors, one or more biological indicators of a user, the one or more biological indicators including a surge in a heart rate;
correlating the one or more biological indicators of the user with the one or more motion signals;
determining that a drink event is detected based on the correlation between the one or more motion signals and the one or more biological indicators, wherein the drink event ends upon a return, based on the one or more motion sensor signals, to a position prior to the drink event being detected; and
estimating a volume of the drink event using an area under a curve of the surge in the heart rate over a baseline heart rate.

2. The method of claim 1, further comprising pre-processing the one or more motion signals using dynamic time warping.

3. The method of claim 1, wherein the at least one motion sensor includes an inertial motion unit, an accelerometer, a magnetometer, and/or a gyroscope.

4. The method of claim 1, further comprising processing the one or more motion signals by a machine learning classification technique.

5. The method of claim 4, wherein the machine learning classification technique includes k-nearest neighbor classifier and/or a neural network classifier.

6. The method of claim 1, wherein the one or more biological sensors includes a thermometer, and the one or more biological indicators includes tissue temperature and ambient temperature.

7. The method of claim 6, wherein the one or more biological indicators includes a decrease in the tissue temperature and/or the decrease in the tissue temperature with respect to the ambient temperature.

8. The method of claim 1, wherein the one or more biological sensors includes a respiration detector, and the one or more biological indicators includes a pause in breathing.

9. The method of claim 1, wherein the one or more biological sensors includes a near-infrared spectrometer, and the one or more biological indicators includes an increase in tissue perfusion and/or blood volume.

10. The method of claim 1, wherein the one or more biological sensors includes a photoplethysmography monitor, and the one or more biological indicators includes a blood oxygen saturation, the heart rate, a heart rate variation, a blood pressure, and/or a respiration rate.

11. The method of claim 1, wherein the one or more biological sensors includes a bioimpedance monitor, and the one or more biological indicators includes tissue hydration variation.

12. The method of claim 1, wherein the one or more biological sensors includes an atmospheric pressure sensor, an altitude sensor, a relative humidity sensor, a microphone, a clock, an event marker, and/or a camera.

13. The method of claim 12, wherein the one or more biological indicators includes atmospheric pressure, altitude, humidity, sounds associated with eating and/or drinking, a time, span of the time, images and/or videos associated with the drinking.

14. The method of claim 1, further comprising:
obtaining, from one or more additional sensors, one or more additional indicators;
correlating the one or more additional indicators with the one or more biological indicators of the user and the one or more motion signals;
determining that the drink event is detected based on the correlation between the one or more additional indicators, the one or more motion signals, and the one or more biological indicators.

15. The method of claim 14, wherein the one or more additional sensors includes a global position system component, and the one or more additional indicators includes a physical location.

16. The method of claim 15, wherein the physical location includes a restaurant and/or a bar.

17. The method of claim 15, wherein the physical location is determined by a calendar, events and/or postings on one or more social media applications, ambient light, UV exposure, humidity, altitude, images, videos, and/or previously visited locations.

* * * * *